US008563789B2

(12) United States Patent
Elsheikh et al.

(10) Patent No.: US 8,563,789 B2
(45) Date of Patent: Oct. 22, 2013

(54) PROCESS FOR THE MANUFACTURE OF HYDROFLUOROOLEFINS

(75) Inventors: Maher Y. Elsheikh, Wayne, PA (US); Philippe Bonnet, Lyons (FR); Benjamin Bin Chen, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 160 days.

(21) Appl. No.: 13/297,557

(22) Filed: Nov. 16, 2011

(65) Prior Publication Data

US 2012/0078020 A1 Mar. 29, 2012

Related U.S. Application Data

(63) Continuation-in-part of application No. 12/664,205, filed as application No. PCT/US2008/068293 on Jun. 26, 2008, now Pat. No. 8,076,521.

(60) Provisional application No. 60/946,406, filed on Jun. 27, 2007.

(51) Int. Cl.
*C07C 17/20* (2006.01)

(52) U.S. Cl.
USPC ............................ 570/160; 570/123; 570/153

(58) Field of Classification Search
None
See application file for complete search history.

(56) References Cited

U.S. PATENT DOCUMENTS

| | | | | |
|---|---|---|---|---|
| 5,616,819 | A * | 4/1997 | Boyce et al. | 570/167 |
| 5,731,481 | A | 3/1998 | Cherminal et al. | |
| 5,877,359 | A | 3/1999 | Elsheikh | |
| 5,895,825 | A * | 4/1999 | Elsheikh et al. | 570/167 |
| 6,752,459 | B2 | 6/2004 | Deisig | |
| 7,485,598 | B2 | 2/2009 | Elsheikh et al. | |
| 8,076,521 | B2 * | 12/2011 | Elsheikh et al. | 570/160 |
| 2007/0197842 | A1 * | 8/2007 | Mukhopadhyay et al. | 570/155 |
| 2009/0030244 | A1 | 1/2009 | Merkel et al. | |
| 2010/0331583 | A1 | 12/2010 | Johnson et al. | |
| 2011/0155942 | A1 | 6/2011 | Pigamo et al. | |
| 2011/0160497 | A1 | 6/2011 | Deur-Bert et al. | |
| 2011/0218369 | A1 | 9/2011 | Elsheikh et al. | |

FOREIGN PATENT DOCUMENTS

| | | | |
|---|---|---|---|
| EP | 0 939 071 | A1 | 1/1999 |
| EP | 0 939 071 | B1 | 7/2003 |
| JP | 2004043410 | A | 2/2004 |

* cited by examiner

*Primary Examiner* — Sudhakar Katakam
(74) *Attorney, Agent, or Firm* — Steven D. Boyd

(57) ABSTRACT

In this invention we are disclosing a process for the synthesis of hydrocchlorofluoro olefins (HCFO) and/or hydrofluoroolefins (HFO). The process is based on the steps of fluorination of hydrochloropropenes or hydrochloropropanes to form hydrochlorofluoropropenes and/or hydrofluoropropenes, followed by gas phase, catalytic fluorination of the hydrochlorofluoropropenes to form hydrofluoropropenes.

19 Claims, No Drawings

PROCESS FOR THE MANUFACTURE OF HYDROFLUOROOLEFINS

The present application is a continuation-in-part of U.S. application Ser. No. 12/664,205 filed Dec. 11, 2009, which claims priority to Patent Cooperation Treaty application serial number PCT/US08/68293 filed Jun. 26, 2008 which claims priority to U.S. Provisional Patent Application Ser. No. 60/946,406 filed Jun. 27, 2007.

FIELD OF THE INVENTION

The present invention relates to a process for the manufacture of a hydrofluoropropenes. More particularly, the present invention relates to a process for manufacturing the hydrofluoropropene 1,1,1,2-tetrafluoropropene (HFO-1234yf) from 1,1,2,3-tetrachloropropene (HCC-1230xa), and/or its isomer 1,1,1,2-tetrachloropropene (HCC-1230xf). The starting materials for the process can be the tetrachloropropene(s) themselves or their precursor materials such as 1,1,1,2,3-pentachloropropane (HCC-240db), 1,1,2,2,3-pentachloropropane (HCC-240aa) and/or 1,1,1,2,2-pentachloropropane (HCC-240ab). The process comprises two steps, the first step being a liquid phase or gas phase fluorination in the presence or absence of homogenous or heterogeneous catalyst to form the intermediate product the hydrochlorofluoropropene 1,1,1-trifluoro-2-chloropropene (HCFO-1233xf), followed by a second step comprising a catalyzed gas phase fluorination of the 1,1,1-trifluoro-2-chloropropene (HCFO-1233xf) to form the desired product 1,1,1,2-tetrafluoropropene (HFO-1234yf) and co-products, primarily 1,1,1,2,2-pentafluoropropane (HFC-245cb). The co-products can be recycled back to the second, gas phase reaction. The catalyst of the second step is preferably a chromium based catalyst such as $CrO_mF_n$, with 1.5<m<3 and 0<n<3, supported or unsupported.

BACKGROUND OF THE INVENTION

The Montreal Protocol for the protection of the ozone layer, signed in October 1987, mandates the phase out of the use of chlorofluorocarbons (CFCs). Materials more "friendly" to the ozone layer, such as hydrofluorocarbons (HFCs) eg HFC-134a replaced chlorofluorocarbons. The latter compounds have proven to be green house gases, causing global warming and were regulated by the Kyoto Protocol on Climate Change. The emerging replacement materials, hydrofluoropropenes, were shown to be environmentally acceptable i.e. have zero ozone depletion potential (ODP) and acceptable, low GWP. The present invention is directed towards a process for manufacturing of hydrofluoroolefins such as hydrofluoropropenes and/or hydrochlorofluoroolefins. The process of the present invention is based on a two-step reaction process including a gas or liquid phase, fluorination followed by a catalytic gas phase fluorination to produce the desirable fluoroolefins.

Methods of preparing hydrofluoroalkenes are known. For example, WO2007/079431 discloses processes for the production of fluorinated olefins, including hydrofluoropropenes. The processes which are broadly described as a single reaction or two or more reactions involve fluorination of compounds of the formula $C(X)_mCCl(Y)_nC(X)_m$ to at least one compound of formula $CF_3CF{=}CHZ$, where each X, Y and Z is independently H, F, Cl, I or Br and each m is independently 1, 2 or 3 and n is 0 or 1. The examples and preferred embodiments disclose multi-step processes such a reaction sequence wherein a feedstock of 1,1,2,3 tetrachloropropene (1230xa) is fluorinated in a catalyzed, gas phase reaction to form a compound such as 2-chloro-3,3,3-tri-fluoropropene (HCFO-1233xf). The 2-chloro 3,3,3-tri-fluoropropene is then converted to 2-chloro-2,3,3,3-tetrafluoropropane (HCFC-244bb) via a liquid phase, catalyzed reaction. Followed by dehydrochlorination of the 2-chloro-2,3,3,3-tetrafluoropropane (HCFC-244bb) to 2,3,3,3-tetrafluoropropene (HFO-1234yf) via a catalyzed, gas phase reaction.

SUMMARY OF THE INVENTION

The present invention provides a process for producing the hydrofluoropropene 1,1,1,2-tetrafluoropropene (HFO-1234yf) from "feedstock" such as tetrachloropropenes, 1,1,2,3 tetrachloropropene (HCO-1230xa) and/or 1,1,1,2 tetrachloropropene (HCO-1230xf) or pentachloropropanes, HCC-240db, HCC-240aa and/or HCC-240ab which are precursors of the tetrachloropropenes. The process of the present invention comprises the steps of:

a) liquid phase or gas phase fluorination of tetrachloropropene (which may be formed via gas phase fluorination of pentachloropropane), in the presence or absence of homogenous or heterogeneous catalyst; to form the intermediate product HCFO-1233xf and thereafter b) gas phase, catalytic fluorination of the intermediate HCFO-1233xf to form the hydrofluoropropene product 1,1,1,2-tetrafluoropropene (HFO-1234yf). The reaction sequence can be summarized as:

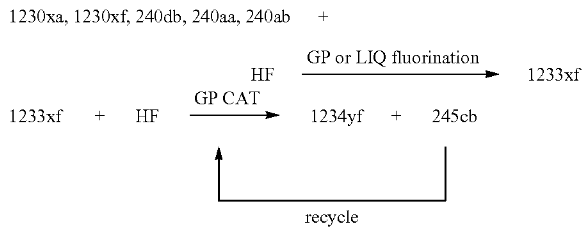

DETAILED DESCRIPTION OF THE INVENTION

The first step of the present invention relates to liquid or gas phase fluorination of a hydrochloropropene such as HCO-1230xa or HCO-1230xf, in the absence or the presence of a catalyst selected from homogeneous or heterogeneous catalysts to form the hydrochlorofluoropropene, 2-chloro-3,3,3-trifluoropropene (HCFO-1233xf). The hydrochloropropene can be formed via the gas phase fluorination of a hydrochloropropane such as HCC-240db, HCC-240aa or HCC-240ab. The fluorination of the hydrochlororpropane can be a separate step or can occur in situ with the gas phase fluorination of the hydrochloropropene.

HCO-1230xf, can be isomerized in the presence of acid catalyst to produce HCO-1230xa, as shown in Scheme 1

Scheme 1. Isomerizaton of 1230xf to 1230xa

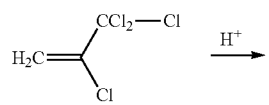

-continued

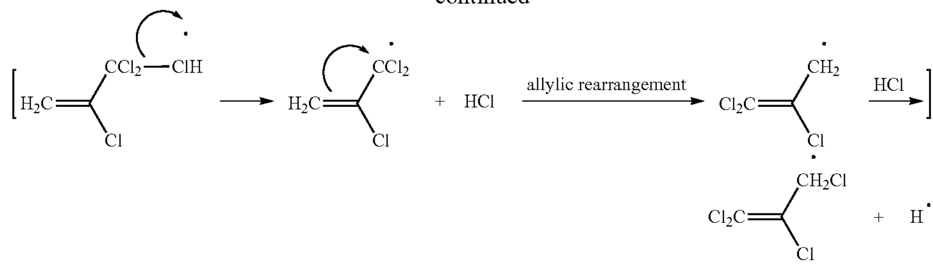

HCO-1230xa, or its isomer HCO-1230xf, can be obtained by thermal dehydrochlorination of hydrochlorocarbons such as HCC-240db, HCC-240aa and/or HCC-240ab, as shown in Scheme 2.

Scheme 2. Dehydrochlorination of HCC-240db, HCC-240aa and/or HCC-240ab to HCO-1230xa.

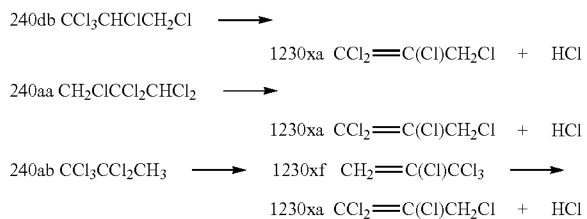

In one embodiment, the first step of the process of the present invention comprises the liquid phase fluorination of tetrachloropropene with HF, preferably utilizing no catalyst. The HF to tetrachloropropene molar ratio is preferably from about 3 to 1 to about 500 to 1, more preferably from about 10 to 1 to about 200 to 1. The reaction temperatures can vary from about 20° C. to about 400° C., preferably from about 100° C. to about 350° C. Operating pressures can range from about 10 to about 900 psia, preferably from about atmospheric pressure to about 700 psia. Residence time is normally from about ¼ to 24 hours, preferably from about ½ hour to about 2 hours. Any unreacted feedstock can be easily separated from the desired product due to the large difference in their boiling points. The reaction vessel is preferably constructed from material resistant to HF, such as 316L stainless steel, INCONEL® or HASTELLOY®. The reaction can be carried out via a continuous or batch process.

The principal by-product of this reaction is hydrogen chloride (HCl), which may be removed by conventional means known in the art, such as absorption or distillation. After removal of HCl, the product stream contains the desired hydrochlorofluoropropene product, HCFC-1233xf, and may include co-products and unreacted starting materials including but not limited to: HF, pentafluoropropanes such as 245cb and chlorotetrafluoropropanes such as 244bb. This stream with or without separation of the co-products provides the feed stream for the second reaction step.

Optionally, the first step liquid phase fluorination can be carried out in the presence of a catalyst. The catalyst can be a homogeneous fluorination catalyst selected from the catalysts such as $SbCl_5$, $TiCl_4$, and $SnCl_4$. The level of homogeneous fluorination catalyst used can vary between 0.1-10 mole % of the organic present. The homogeneous fluorination catalyst is first activated with HF where HCl co-product is vented. The process of activation can be carried out at temperature varied between room temperature to 200° C., preferably between room temperature to 100° C. The liquid phase fluorination can be carried out continuously or using batch conditions. When antimony catalyst is used, a low level of chlorine gas varied between about 1-10 mole % can be provided to extend catalyst life.

In an alternative embodiment, the first step is carried out in the gas phase and a heterogeneous catalyst is used. This catalyst can be selected from supported or unsupported chromium based catalyst. A co-catalyst selected from the group nickel, zinc, cobalt or magnesium can be used. The level of co-catalyst can be varied between 1-50 weight % of the catalyst, preferably between 5-10 weight %. The incorporation of co-catalyst can be via processes known in the art such as adsorption from aqueous or non aqueous solution, intimate physical mixing of the co-catalyst and catalyst or coprecipitation from aqueous or non aqueous solutions. When a supported catalyst is used, the support can be selected from the group activated carbon, graphite, fluorinated graphite, alumina, fluorinated alumina, chromia, fluorinated chromia, magnesia and fluorinated magnesia. The preparation of supported catalyst can be via processes known in the art such as adsorption from aqueous or non-aqueous solutions, coprecipitation from aqueous or non-aqueous solution or by mixing of the support and catalyst/co-catalyst mixture.

When a chromium based catalyst such as $Cr_2O_3$ is used in the first step it is subjected to an HF activation in the presence or absence of co-carrier such as nitrogen or air. In a typical activation process, in a first step, the catalyst is dried at temperature between 100° and 200° C., in the presence of a carrier gas such as nitrogen. After drying, the catalyst is activated with HF in the presence of carrier gas such as nitrogen or air. Typically, the HF activation step can be started at about 100° C., using a diluted mixture of HF in nitrogen or air mixture, which is gradually increased in such a way so as to maintain the temperature of the catalyst bed below 400° C. The air or nitrogen diluent is then gradually decreased. The reactor pressure is then increased to about the desired reaction pressure, for example 10 to 900 psia, and pure HF is gradually added for another 18 hours. The HF activation step is followed by a second activation step with air in which the catalyst is heated up at approximately 300° to 400° C., preferably between 330° to 360° C. for approximately 24 hours in a stream of dry air. The resulting HF and air activated catalyst preferably has the approximate composition $CrO_mF_n$, with $1.5<m<3$ and $0<n<3$. The activated catalyst preferably has a fluorine content of about 35-40 weight %, a surface area is between 10-100 $m^2/g$, pore volume is between 0.1-1 $m^3/g$, % attrition is preferably between about 1-5% and crushing strength is approximately 20-100 psi.

In an alternative embodiment, the first step of the process can comprise the gas phase fluorination of teterachloropropene with HF, preferably utilizing no catalyst. The processing conditions for the gas phase fluorination, catalyzed and uncatalyzed, are similar to the liquid phase step described above eg; the operating temperature can be varied between 100°-500° C., preferably between 200°-450° C. It is an advantage to use a contact time between 1-100 seconds, preferably between 5-20 seconds. Because HCl is generated as a co-product in the process, it is preferable to operate the process under pressure, between 10-1000 psi and most preferable between atmospheric pressure and 400 psi. A co-feed of an oxygen containing gas such as air is preferred to extend the catalyst life by minimizing the need to shut down the process to remove carbonous deposits. The molar ratio of HF to organic can be varied between 1/1 to 100/1 with the molar ratio of HF/organic preferably between 5/1 to 40/1.

The tetrachloropropene starting material of the present invention, HCO-1230xa or HCO-1230xf, can be prepared by the gas phase dehydrochlorination of pentachloropropanes such as HCC-240db, HCC-240aa and/or HCC-2240ab in the gas phase in the presence of a catalyst. The catalyst is preferably a $Cr^3$ based catalyst, supported or unsupported. The catalyst is preferably activated as described above. A co-catalyst selected from the group nickel, zinc and magnesium may be used. The operating temperature can be varied between 200-500 C and is preferably between 200-400 C. The operating pressure can be varied within the range 100-1000 psi, and is preferably between 200-400 psi. The molar ratio of HF to organic feed is preferably between 5/1 to 40/1, and the contact time is between 10-100 seconds. To run the process for extended period of time without catalyst deactivation, it is advantageous to use a molar ratio of oxygen to the organic feed of between 1-10 volume %. The oxygen can be feed as pure oxygen or oxygen containing gas such as air or a mixture of oxygen and nitrogen.

The second reaction step of the present invention relates a gas phase, catalytic fluorination of the hydrochlorofluoropropene HCFO-1233xf from the first reaction step, to form the hydrofluoropropene 1,1,1,2-tetrafluoropropene (HFO-1234yf) and co-products, primarily HCC-245cb. The reaction sequence of the second step can be summarized as:

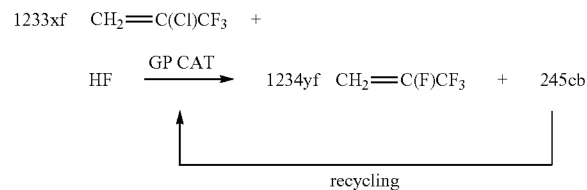

The second step involves contacting the hydrochlorofluoropropene HFO-1233xf with HF under conditions sufficient to produce the hydrofluoroolefin 1,1,1,2-tetrafluoropropene (HFO-1234yf). The HF:hydrochlorofluoropropene molar ratio is typically from about 0.5:1 to 40:1, and is preferably at least about 1:1 to enhance conversion and preferably no more than about 10:1 in order to produce lower levels of HF excess, which are recovered downstream. Temperatures of from about 250° C. to about 600° C. are typically used, preferably from about 300° C. to about 500° C. Pressures are typically from about atmospheric to about 400 psi, preferably from about 50 to 200 psi. The process is preferably carried out at a contact time between 1-100 seconds in the presence of oxygen or oxygen containing gas such as air, using a 1-200 volume % of oxygen based upon the 1233xf feed. Co-products formed such as 245cb and/or 244bb can be recycled.

A variety of fluorination catalysts can be used, such as chromium-based catalyst, which chromium-based catalyst is either unsupported or supported. When supported, the support is selected from fluorinated alumina, activated carbon and the like. The chromium catalyst is used alone or in the presence of a co-catalyst such as zinc, magnesium, cobalt or nickel. Three preferred chromium catalysts are pure chromium oxide, chromium/zinc with zinc as a co-catalyst, chromium/nickel with nickel co-catalyst and chromium/nickel supported on fluorinated alumina. Preparation of this latter catalyst being disclosed, for example, in U.S. Pat. No. 5,731,481. The chromium-based catalysts are preferably activated before use, in a two step procedure as described above.

The reaction product of the second fluorination step will include, in addition to the desired hydrofluoropropene, some unreacted hydrochlorofluoropropene (HCFC-1233xf), pentafluoropropane (HFC-245cb) and monochlorotetrafluoropropane (HCFC-244bb). These byproducts can be separated from the desired hydrofluoropropene in a series of two or more separation columns with the HFC-245cb major by product being recycled to the second gas phase fluorination reaction or catalytically dehydrofluorinated to 1234yf in a separate gas phase reactor, using the same catalyst formulation used in the second step.

The tetrachloropropene feedstock of the present invention can be formed via variety of ways as would be know by a person skilled in the art.

EXAMPLES

Examples 1

Uncatalyzed liquid phase fluorination of 1,1,2,3 tetrachloropropene (HCO-1230xa) to 2-chloro-3,3,3-trifluoropropene (HCFO-1233xf).

$$CCl_2{=}CCl(CH_2Cl)+3HF \rightarrow CF_3CCl{=}CH_2+3HCl$$

0.28 moles of HCO-1230xa can be loaded into a 300 ml Hastelloy C autoclave equipped with gas inlet valve, mechanical stirrer and an outlet cooling tower. 3.5 moles of HF gas can be condensed in the autoclave. The reaction mixture would be gradually heated up to 120° C., with continuous stirring for approximately ½ hour. Excessive gas pressure resulted from the formation of HCl can be vented through a 400 psi pressure relief valve on the cooling tower. The high boiling material would be trapped at room temperature. The volatile organic products could be dried over anhydrous calcium sulfate and collected in a cold trap. Nearly 0.28 moles of the 2-chloro-3,3,3-trifluoropropene product, would be found in the cold trap. Examples 1, 2 and 3, summarized in Table 1, were calculated based upon comparable reactions with closely related materials.

TABLE 1

Summary of the results, uncatalyzed liquid phase fluorination of 1230xa to 1233xf

| Example | 1 |
|---|---|
| Temperature ° C. | 100 |
| Pressure psia | 300 |
| Mole Ratio HF/1230za | 166 |
| Residence time, hours | 5 |
| % Conversion | 100 |

TABLE 1-continued

| Summary of the results, uncatalyzed liquid phase fluorination of 1230xa to 1233xf | |
|---|---|
| Example | 1 |
| 1230xa | |
| % 1234yf | 0.25 |
| % 245cb | 0.16 |
| % 1233xf | 97.2 |
| Other | 2.39 |

1234yf is $CF_3CF{=}CH_2$
245cb is $CF_3CF_2CH_3$
1233xf is $CF_3CCl{=}CH_2$
244bb is $CF_3CFClCH_3$

Examples 2-4

Gas phase fluorination of HCO-1233xf at high temperature.

An activated catalyst, 15 cc, could be loaded into a vertical fix bed reactor (20 inches by 1 inch Hastelloy C). HF could be fed as a liquid, and converted to a gas using vaporizer. HCO-1233xf could be fed to the fix bed reactor using a syringe pump and heated up to 365° C. The reaction would be run at a pressure of between 42-162 psi. Table 3 summarizes the calculations of expected results using a variety of molar ratio of HCO-1233xf/HF and contact times based upon comparable reactions with closely related materials.

TABLE 3

| Summary of fluorinating 1233xf to 1234yf, using unsupported $Cr_2O_3$ catalyst | | | |
|---|---|---|---|
| Example | 2 | 3 | 4 |
| Temp ° C. | 365 | 365 | 365 |
| Pressure psia | 48.5 | 48.5 | 169 |
| $O_2$/1233xf molar ratio | 0.5 | 0.5 | 0.5 |
| HF/1233xa Molar Ratio | 10.6 | 21.1 | 21.1 |
| Contact Time sec. | 3.9 | 4 | 14 |
| % Conversion | 54.8 | 64.1 | 73.6 |
| % 1234yf | 58.3 | 56.4 | 40.6 |
| % 245cb | 36.6 | 36.5 | 59.4 |
| % 244bb | 5.1 | 7.1 | 0 |

1234yf is $CF_3CF{=}CH_2$
245cb is $CF_3CF_2CH_3$
244bb is $CF_3CFClCH_3$

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

The invention claimed is:

1. A process for producing 1,1,1,2-tetrafluoropropene, comprising the steps of:

a) fluorinating tetrachloropropene to form 2-chloro-3,3,3-trifluoropropene and HCl and first co-products in the presence of a catalyst selected from the group consisting of homogeneous fluorination catalyst selected from the group consisting of $SbCl_5$, $TiCl_4$, $SnCl_4$ and heterogenous catalyst comprising a supported or unsupported chromium catalyst, said heterogenous catalyst optionally further comprising a co-catalyst selected from the group consisting of nickel, zinc, cobalt and magnesium and thereafter b) fluorinating said 2-chloro-3,3,3-tri-fluoropropene, in a gas phase, in the presence of a catalyst selected from the group consisting of supported chromium catalyst, unsupported chromium catalyst and mixtures thereof said chromium catalyst optionally further comprising a co-catalyst selected from the group consisting of nickel, cobalt and magnesium, to form 1,1,1,2-tetrafluoropropene and second co-products.

2. The process of claim 1 wherein the step a) of fluorinating a tetrachloropropene comprises contacting the tetrachloropropene with hydrogen fluoride in the gas phase or the liquid phase.

3. The process of claim 1 further comprising the step of separating HCl from said 2-chloro-3,3,3-tri-fluoropropene and HCl and first co-products prior to fluorinating the 2-chloro-3,3 3-tri-fluoropropene.

4. The process of claim 1 wherein said first co-products comprise pentafluoropropane and chlorotetrafluoropropane.

5. The process of claim 4 wherein said pentafluoropropane comprises 1,1,1,2,2-pentafluoropropane and said chlorotetrafluoropropane comprises 1,1,1,2-tetrafluoro-2-chloropropane.

6. The process of claim 1 further comprising the step of separating said second co-products from said 1,1,1,2-tetrafluoropropene.

7. The process of claim 6 further comprising the step of recycling said separated second co-products to step b.

8. The process of claim 1 wherein said second co-products comprise pentafluoropropane and chlorotetrafluoropropane.

9. The process of claim 8 wherein said pentafluoropropane comprises 1,1,1,2,2-pentafluoropropane and said chlorotetrafluoropropane comprises 1,1,1,2-tetrafluoro-2-chloropropane.

10. The process of claim 2 wherein the ratio of tetrachloropropene to hydrogen fluoride ranges from about 1 to 3 to about 1 to 500.

11. The process of claim 1 wherein the ratio of tetrachloropropene to hydrogen fluoride ranges from about 1 to 10 to about 1 to 200.

12. The process of claim 1 wherein the step of fluorinating the 2-chloro-3,3,3-tri-fluoropropene in a gas phase, in the presence of a catalyst comprises contacting said 2-chloro-3,3,3-tri-fluoropropene with hydrogen fluoride.

13. The process of claim 1 wherein said catalyst is activated prior to use.

14. The process of claim 13 wherein said catalyst is activated at a temperature between 200° and 400° C. in a two step process comprising first contacting with HF followed by contacting with air to produce catalyst of the formula such as $CrO_mF_n$, with $1.5<m<3$ and $0<n<3$.

15. The process of claim 1 wherein said tetrachloropropene is prepared via gas phase fluorination of one or more pentachloropropanes.

16. The process of claim 1 wherein said step of fluorinating tetrachloropropene is carried out in the liquid phase in the presence of a homogenous catalyst.

17. The process of claim 1 wherein said step of fluorinating said tetrachloropropene is carried out in the gas phase in the presence of a heterogenous catalyst.

18. The process of claim 1 wherein said tetrachloropropene is selected from the group consisting of 1,1,1,2-tetrachloropropene, 1,1,2,3-tetrachloropropene and mixtures thereof.

19. The process of claim 18 further comprising the step of isomerizing 1,1,1,2-tetrachloropropene, in the presence of an acid catalyst, to produce 1,1,2,3-tetrachloropropene.

* * * * *